United States Patent [19]

Park et al.

[11] Patent Number: 4,528,272

[45] Date of Patent: Jul. 9, 1985

[54] FERMENTATION OF BILE

[75] Inventors: Robert J. Park, Birkdale; Raymond A. Leppik, Toowong, both of Australia

[73] Assignee: Commonwealth Scientific and Industrial Research Organization, Campbell, Australia

[21] Appl. No.: 597,813

[22] PCT Filed: Feb. 13, 1981

[86] PCT No.: PCT/AU81/00017

§ 371 Date: Oct. 22, 1981

§ 102(e) Date: Oct. 22, 1981

[87] PCT Pub. No.: WO81/02427

PCT Pub. Date: Sep. 3, 1981

Related U.S. Application Data

[63] Continuation of Ser. No. 314,837, Oct. 22, 1981, abandoned.

[51] Int. Cl.$^3$ .................. C12P 33/16; C12R 1/38; C12R 1/365
[52] U.S. Cl. ..................... 435/55; 435/874; 435/872
[58] Field of Search .......................... 435/55

[56] References Cited

U.S. PATENT DOCUMENTS 2,960,513 11/1960 Thoma et al.
3,023,229 2/1962 Muir et al.

(List continued on next page.)

FOREIGN PATENT DOCUMENTS 45981 10/1979 Australia.
0008214 8/1980 European Pat. Off.
0014991 9/1980 European Pat. Off.
2408621 6/1979 France.

OTHER PUBLICATIONS

Barnes et al., Tetrahedron, vol. 32, No. 1, pp. 89–93 (1976).
Hossain et al., Steroids, vol. 27, No. 5, pp. 603–608 (1976).

(List continued on next page.)

Primary Examiner—Alvin E. Tanenholtz
Attorney, Agent, or Firm—Cushman, Darby & Cushman

[57] ABSTRACT

This invention relates to a process for the fermentation of bile which includes the step of cultivating one or more aerobic microorganisms which have the ability to selectively degrate bile acids or bile acid conjugates contained in bile. The fermentation is carried out in a cultivation medium containing or consisting of unfractionated bile under aerobic conditions to prepare a compound of the formula wherein ~ is a bond chosen from one which is alpha or beta to the ring, X is chosen from hydrogen, hydroxyl or oxo, ===== may be either a double or single bond, and R is selected from oxo, hydroxy or a propionic acid residue, attached at the 2-position (i.e. $CH_3-CH-COOH$).

The invention also includes within its scope certain compounds as described herein prepared by the process of the invention.

13 Claims, 2 Drawing Figures

U.S. PATENT DOCUMENTS 3,388,042  6/1968  Arima et al. ............................ 435/55
3,560,558  2/1971  Hayakawa et al. ................... 435/244
3,684,656  8/1972  van der Waard ...................... 435/55
4,101,378  7/1978  Nishikawa et al.
4,320,195  3/1982  Hill et al. ................................ 435/55

OTHER PUBLICATIONS

Tenneson et al., FEBS Letters, vol. 91, No. 1, pp. 140–142 (1978).
Arima et al., Agr. and Biol. Chem., vol. 42, No. 2 (1978), pp. 411–416.
Tenneson et al., Bioch. Soc. Trans., vol. 6, No. 5, pp. 975–977 (1976).
Schwarz et al., Folia Microbiologica, vol. 19, No. 2, pp. 156–163 (1974).
Raspe et al., Naturwissenschaften, vol. 48, p. 479 (1961).
Tweit et al., J. of Org. Chem., vol. 27, pp. 3654–3658 (1962).
Heftmann et al., Biochemistry of Steroids, Reinhold Pub. Corp., New York, pp. 79–84 (1960).

TABLE I.
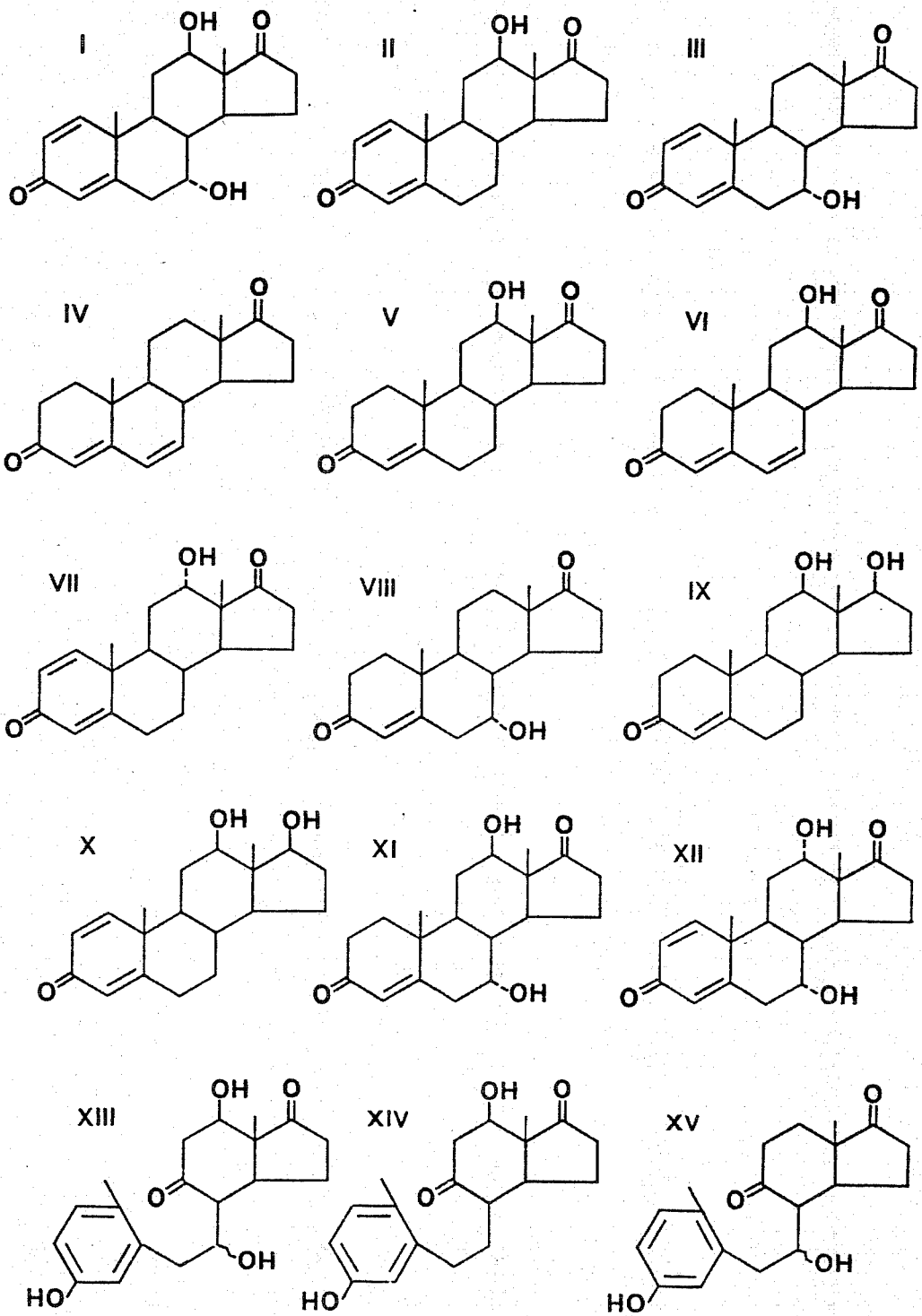

TABLE II.
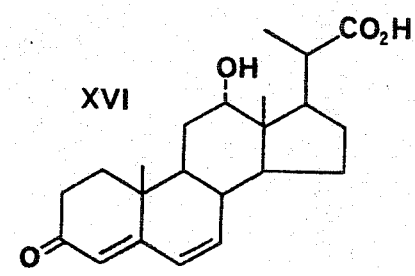
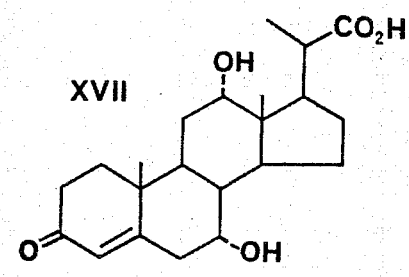
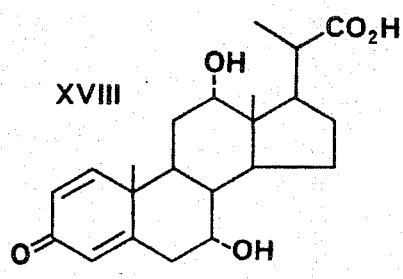
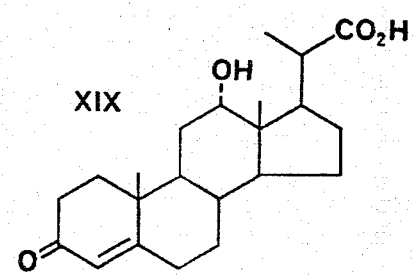
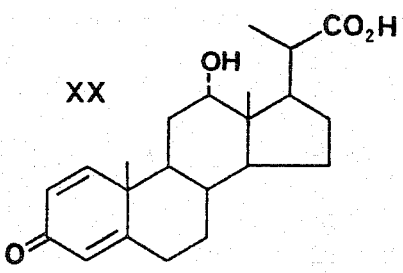
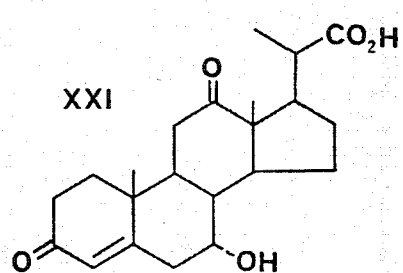
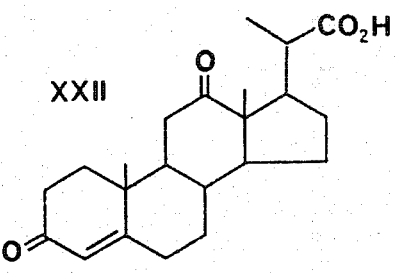
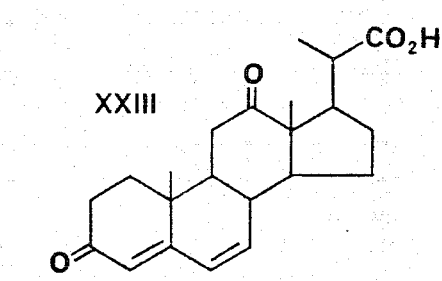

FERMENTATION OF BILE

This is a continuation of application Ser. No. 314,837, filed Oct. 22, 1981 and now abandoned.

This invention relates to the conversion of animal bile to compounds of value as intermediates for the production of pharmaceuticals.

Currently the corticosteroids and other steroid pharmaceuticals are synthesised by lengthy and expensive chemical processes. Materials isolated from bile, such as the bile acids, cholic acid and deoxycholic acid, may be used as intermediates in such processes. Also, it has been reported that the bile acids and their conjugates with taurine and glycine may be microbially transformed into certain steroids. Both the chemical and microbial prior art concerns the treatment of bile components per se. Surprisingly, it has now been found that, as regards microbial transformations, the use of pure compounds as starting materials is unnecessary and, moreover, there are significant advantages in employing unfractionated bile as a substrate for steroid production.

Accordingly, a major aspect of the present invention is the provision of a process for the preparation of steroids which comprises the microbial fermentation of unfractionated bile.

In this specification the term 'unfractionated bile' means bile from which components such as bile acids, bile acid conjugates, proteins and lipids have not been extracted, but it does not exclude bile concentrated by the evaporation of water.

Accordingly, the invention provides a process for the fermentation of bile which includes the step of cultivating one or more aerobic microorganism(s) which has or have the ability to selectively degrade bile acids or bile acid conjugates contained in bile in a cultivation medium containing or consisting of unfractionated bile under aerobic conditions to prepare a compound of the formula

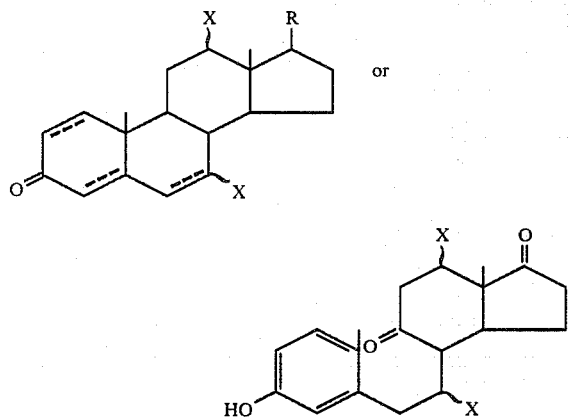

wherein ~ is a bond chosen from one which is alpha or beta to the ring, X is chosen from hydrogen hydroxyl or oxo, --- may be either a double or single bond, and R is selected from oxo, hydroxy, or a propionic acid residue attached at the 2-position (i.e. $CH_3-\underset{|}{CH}-COOH$).

Any suitable aerobic microorganism characterised by its ability to grow aerobically in bile can be used in the process of the invention. Typically, suitable organisms will be adapted to the presence of bile and so, for example, may be found in the vicinity of bile-processing plants or in faeces; they may, however, be adapted to bile utilisation by well known techniques such as mutation, and gene or plasmid transfer.

Species of the genus Pseudomonas have been found to be particularly effective in selectively degrading bile acid conjugates. Thus, under certain conditions Pseudomonas sp. ATCC 31752 can accumulate compounds I–III (as designated in Table I hereinafter) in a cattle or sheep bile fermentation liquor; under other conditions compounds XIII–XV in Table I hereinafter will accumulate, while with different conditions again, other conditions shown in Table I can be obtained. Another Pseudomonas sp. ATCC 31753 is seen to be characterised by its ability to produce mainly acidic compounds such as some of those in Table II.

Most of the compounds shown in Table II hereinafter can be obtained from a cattle or sheep bile fermentation liquor when the active microorganism is Nocardia sp. ATCC 31754 (or the revised genus Rhodococcus sp. ATCC 31754, see Goodfellow and Alderson, J. Gen. Microbiol. 100, 99–122, 1977). Other species of the genera Rhodococcus, Nocardia, Mycobacterium, Arthrobacter, Corynebacterium, Streptomyces, Actinomyces, mutants thereof and any other aerobic microorganisms are within the scope of this invention, provided they possess the ability to selectively degrade the bile acid conjugates of bile in the presence of other bile components.

The invention also includes within its scope novel compounds that may be prepared by the process of the invention. These compounds with reference to Tables I and II hereinafter referred to are compounds V, VI, VIII, IX, X, XI, XIII, XIV, XV and XIX.

As previously intimated, the microbial transformation of sterols is not an unknown art. However, the prior art is distinguished by its reference only to the treatment of purified substances, and while it taught that it was possible to produce useful materials from, for example, relatively cheap plant or animal sterols, previously proposed processes have suffered from serious deficiencies. Thus, U.S. Pat. No. 3,684,657 teaches that the plant sterols or cholesterol can provide androsta-1,4-diene-3,17-dione, and U.S. Pat. No. 4,029,549 teaches that 9α-hydroxy pregn-4-ene-3-one-20α-carboxylic acid can be obtained from similar sterols, but an inherent problem of both processes is the relative insolubility of the subtrates employed, which necessitates the use of dispersants and also limits the amounts which can be used to about 2 g/liter. The present invention, on the other hand, offers the very important advantage that the substrate is so water soluble that the level of substrate that can be easily and successfully employed is more than twenty times than in the case of the plant sterols and cholesterol.

In addition, whereas the prior art processes require the use of extraneous sources of nitrogen, carbon and, sometimes more expensive cofactors, the latter can be omitted from the fermentation media of the present invention since the nonsteroid bile components provide adequate nitrogen, sulphur and other cofactors. The only additional ingredients which would normally be recommended are pH buffering agents, such as phosphates, but these too can be omitted if a relatively slow fermentation rate is acceptable.

A further advantage of the process of this invention derives from the fact that conversion of the bile acid substrate to steroid products occurs at a much faster rate than the steroid conversions of the prior art. This, together with the highly specific nature of the substrate, means that contamination is rarely if ever a problem since contaminating microorganisms have little opportunity to proliferate.

To summarize, the advantages which this invention offers over prior art processes are:
1. The use of a substrate which is inexpensive, widely available and does not require any complicated pretreatment.
2. The use of microorganisms which are particularly vigorous and which will grow well in a bile medium without the need for expensive additives.
3. A substrate which is highly water soluble, and which permits the growth of selected microorganisms at high substrate concentrations.
4. Little risk of contamination by other microorganisms, thus eliminating the need for expensive and time-consuming sterilising procedures.

In performance of the present invention it is usual, but not essential, to include bile in a fermentation medium at a concentration of up to about 10% bile solids. The medium is incubated with a microorganism previously cultured with another, or the same, medium; the medium may contain additional nutrients. Culture with Pseudomonas sp. ATCC 31752 causes the accumulation of compounds I–III in the broth. When cultured with a mutant of one of the other microorganisms, the broth can accumulate any one or more of the compounds I–XXIII. If a wild strain of one of the microorganisms is used, a mixture of products will accumulate, the proportions of which will vary with the time of harvesting the culture.

A suitable point for harvesting the bile culture may be selected by monitoring one or more several parameters such as microbial cell density, adsorption of UV light of a culture filtrate, or chromatographic analysis of the culture filtrate.

The products of the fermentation may be recovered in numerous ways, such as removal of bacterial cells by centrifugation, followed by acidification of the remaining liquor, extraction with a suitable water-immiscible organic solvent and fractionation of the extract by crystallisation or chromatographic means to isolate the desired compounds. However, according to a preferred process of the invention, unwanted bacterial cells are removed by centrifugation, the liquor is percolated through a column of porous polymer beads, which is then washed to remove unwanted inorganic compounds, and the steroid products selectively eluted by treatment of the column with mixtures of water and methanol. The separated products are then purified by recrystallisation from suitable solvents.

Any suitable cultivation temperature may be utilized in the process of the invention. Thus temperatures of from 10° to 45° C. may be used but preferably temperatures of from 20° to 30° C. and more preferably 25° to 30° C. are utilized. Appropriate cultivation times will be apparent from a reading of the following examples.

The following examples are intended to illustrate the invention but are not to be construed as limiting.

EXAMPLE 1

Production of compounds I, II and III from bile with Pseudomonas sp. ATCC 31752.

Cells of Pseudomonas sp. ATCC 31752 are grown at 30° C. in the following sterile medium in a suitable flask as seed innoculum.

Bile concentrate (ca. 70% solids)—5 g
Yeast extract—0.1 g
$K_2HPO_4$—3.5 g
$KH_2PO_4$—1.5 g
$(NH_4)_2SO_4$—2 g
$MgSO_4.7H_2O$—0.1 g
$CaCl_2$—0.01 g
$FeSO_4.7H_2O$—0.001 g
De-ionised water to—1 liter The innoculum medium is sterilised at 120° C. for 20 minutes. The Pseudomonas sp. ATCC 31752 is added to the innoculum from a slope culture. The seed innoculum is grown overnight with aeration, requiring about 12–16 hours growth. This seed culture is innoculated aseptically into a fermenter which contains ten to twenty times the volume of the innoculum of a sterile medium of the following composition, per 10 liters of medium.

Bile concentrate (ca. 70% solids)—100 g
$K_2HPO_4$—35 g
$KH_2PO_4$—15 g
$(NH_4)_2SO_4$—20 g
Silicone antifoam—2 ml
Tap water to—10 liters The innoculated bile medium is incubated at 30° C. with aeration at 60 ml per minute for 7 hours. The aeration is then reduced to 40 ml/minute for a further 40 hours, the point of harvesting being decided by the attainment of maximum absorption of a filtrate of the sample from the medium at 240 nm. The transformed bile is then chilled to <5° C. and centrifuged to remove bacterial cells. The supernatant liquor is passed through a bed of a polymeric, non-ionic adsorbent (polystyrenedivinylbenzene copolymer is suitable) to adsorb organic materials. The bed of adsorbent is then washed with de-ionised water until the eluate is free from phosphate and then treated with a mixture in gradient form of water-methanol.

From eluate comprising 50% of methanol in water a crystalline product A (8.1 g) is obtained on evaporation of the organic solvent and cooling. After removal of these crystals the aqueous portion is extracted with n-butanol and provides, on evaporation of the butanol layer, a further crystalline material B (8.1 g). From eluate comprising 100% methanol is obtained, after removal of solvent, a further solid material C (9.1 g).

Crystalline material A is seen by thin layer chromatography (t.l.c.) to be nearly pure compound I and on recrystallisation from NN-dimethylformamide (DMF) provides the 7α,12β-dihydroxyandrosta-1,4-diene-3,17-dione which decomposes without melting above 270° C. Product B is similarly seen to contain mainly I, which is purified by recrystallising as above.

Product C is seen by t.l.c. to be a mixture of compounds II and III. The product is taken up in methylene chloride and chromatographed on silica gel using methylene chloride and DMF as eluents. From eluate comprising 3% DMF in methylene chloride is obtained a product which is recrystallised from methanol to provide compound II, 12β-hydroxyandrosta-1,4-diene-3,17-dione, melting point 224°–226° C. (4.6 g). From eluate comprising 5% DMF in methylene chloride is obtained a product recrystallised from methanol to give compound III, 7α-hydroxyandrosta-1,4-diene-3,17-diene, melting point 291°-293° C. (1.2 g).

EXAMPLE 2

Production of compounds I-XII and XVI from bile with Pseudomonas sp. ATCC 31752.

The seed innoculum of Pseudomonas sp. ATCC 31752 is prepared exactly as in Example 1. The bile medium contains the following, per 10 liters of medium.

Bile concentrate (ca. 70% solids)—1 kg
$K_2HPO_4$—35 g
$KH_2PO_4$—15 g
$MgSO_4.7H_2O$—2 g
$(NH_4)_2SO_4$—50 g
Silicone antifoam—2 ml
Tap water to—10 liters The innoculated bile medium is incubated at 30° C. with aeration at 450 ml per minute for 22 hours and then 300 ml per minute for a further 27 hours, the point of harvesting being determined by the disappearance of bile acids and conjugates from a sample of the medium, assessed by t.l.c. or, preferably, by high performance liquid chromatography using 60 to 75% aqueous methanol on a C18 reverse phase analytical column at a flow rate around 30-40 ml/hr. The transformed bile is treated as in Example 1 and applied to the polymeric non-ionic adsorbent as in that Example.

The resulting eluates are evaporated as in Example 1, to give a total of 148.5 g of product. The sludge remaining from centrifuging the fermenter liquor is extracted with hot n-butanol and produces a further crystalline product D (33.4 g) by evaporating the butanol. These products A-D are seen by t.l.c. to contain the compounds I-XII and XVI.

Product C is seen to contain compounds of low polarity. A portion (26 g) is chromatographed on silica gel using a gradient of acetone in chloroform to separate the components. From the eluate comprising 10% acetone a fraction containing IV is obtained. This is re-chromatographed on silica gel with equal parts of hexane and ethyl acetate as eluent and provides a fraction which on recrystallising the product from aqueous ethanol gives pure IV, seen to be androsta-4,6-diene-3,17-dione, melting point 171.5°-172.5° C. (0.65 g). Similarly an eluate comprising 15% acetone is seen to contain a mixture of products, V and VI. On re-chromatography as above with hexane-ethyl acetate the compound V elutes first and on recrystallising this product from aqueous ethanol gives pure V, shown to be 12β-hydroxyandrost-4-ene-3,17-dione, melting point 169°-70° C. (8.2 g). The product VI elutes soon after and on recrystallising the product from aqueous ethanol gives pure VI, 12β-hydroxyandrosta-4,6-diene-3,17-dione, melting point 195°-6° C. (0.75 g). Similarly, an eluate comprising 20-25% acetone is seen to contain a mixture of II and VII. On re-chromatography as before, component II elutes first and then VII. On recovering this latter component and re-crystallising from aqueous ethanol gives pure VII, seen to be 12α-hydroxyandrosta-1,4-diene-3,17-dione melting point 202°-3° C. (0.34 g). Similarly the eluate comprising 30-35% acetone is seen to contain III and VIII. On re-chromatography of this product with ethyl acetate-hexane the first component eluting is VIII. On recovering this product and recrystallising from aqueous ethanol pure VIII is obtained, shown to be 7α-hydroxyandrost-4-ene-3,17-dione melting point 248°-50° C. (0.22 g). Similarly the eluate comprising 35-40% acetone is seen to contain IX and X, eluting separately. The first product is recovered and on recrystallising from aqueous ethanol pure IX is obtained shown to be 12β,17β-dihydroxyandrost-4-ene-3,17-dione melting point 118°-19° C. (1.6 g). The second product is also recovered and on recrystallising from aqueous ethanol pure X is obtained, shown to be 12β,17β-dihydroxyandrosta-1,4-diene-3-one, melting point 174°-5° C. (0.79 g).

Product A is seen by t.l.c. to comprise compounds, I, XI and XII with some acidic material, which is removed by extraction with $Na_2CO_3$ in water. A portion of the neutral portion of product A (4.3 g) was dissolved in chloroform and chromatographed on silica gel with chloroform and DMF as eluents. From an eluate comprising 6% DMF a crystalline product is obtained which on recrystallising from aqueous ethanol affords white crystals of XI shown to be 7α,12β-dihydroxyandrost-4-ene-3,17-dione decomposing at 238° C. (0.64 g).

From the eluate comprising 10% DMF in chloroform is obtained a crystalline product which on recrystallising from aqueous ethanol affords white crystals of XII, seen to be 7α,12α-dihydroxyandrosta-1,4-diene-3,17-dione (0.3 g), which decomposes without melting at 290° C.

The acidic material from Product A is recovered by extraction of the $Na_2CO_3$ solution with chloroform after addition of an excess of acetic acid and evaporation of the solvent. This acidic material (11.5 g) is converted to the methyl esters with excess diazomethane and seen to contain the methyl ester of compound XVI. These esters are dissolved in methylene chloride and chromatographed on silica gel with ethyl acetate and methylene chloride as solvents. From an eluate comprising 55% ethyl acetate in methylene chloride is obtained a crude crystalline product rich in XVI. This product is rechromatographed on silica gel using hexane and ethyl acetate as solvents in the presence of 0.2% acetic acid. From an eluate comprising 50% ethyl acetate a crystalline product is obtained and on recrystallising from ethanol gives pure methyl ester of XVI shown to be methyl 12α-hydroxy-3-oxopregna-4,6-diene-20-carboxylate, melting point 182.5°-4° C. (0.34 g).

EXAMPLE 3

Production of compounds I, III, XIV-XV from bile with Pseudomonas sp. ATCC 31752.

The seed innoculum of Pseudomonas sp. ATCC 31752 and bile medium are prepared exactly as in Example 1. Sterile air is introduced into the 10 liters of innoculated medium at 400 ml/min for 3 hours and aeration then reduced to 150 ml/min for a further 24 hours at which time production of compounds I and II are at a maximum. Aeration is then increased to 600 ml/min for a further 4 hours. The point of harvesting is determined by the disappearance of compound II from the medium and the rapid reduction of quantity of compound I together with the appearance of new products, as assessed by HPLC or t.l.c., or by the rapid reduction of absorbance at 240 nm and attaining a maximum absorbance at 280 nm in clear filtrates of the medium. In the latter instance harvesting is selected when 240 nm absorbance is about 1/5 of the maximum value. The transformed bile is treated as in Example 1 to recover products of the microbial transformation of the bile and conjugates. Product A is obtained on evaporation of the solvent from a 50% aqueous methanol eluate of the polymeric non-ionic adsorbent column, product B from 75% methanol eluate and product C from 100% methanol eluate.

Product A is seen by t.l.c. to contain I and XIII. A portion (1.5 g) is dissolved in methylene chloride and applied to a column of silica gel with solvents methylene chloride and DMF. From an eluate comprising 5% DMF in methylene chloride a product is obtained which on recrystallising from aqueous methanol affords pure crystals of XIII, shown to be 3,7,12β-trihydroxy-9,10-seco-androsta-1,3,5(10)-triene-9,17-dione, melting point 158°–159.5° C. (0.68 g).

Product C (4 g) is seen by t.l.c. to contain some XIV and XV with II as the main component. The product is dissolved in methylene chloride and applied to a column of silica gel with solvents of equal parts of ethyl acetate and hexane. The first component eluted on recrystallising from ethanol affords white crystals of XIV shown to be 3,12β-dihydroxy-9,10-seco-androsta-1,3,5(10)-triene-9,17-dione, melting point 169°–70° C. (0.13 g). The next component eluted affords partially crystalline material (0.11 g) which is consistent in chemical structure with XV 3,7-dihydroxy-9,10-seco androsta-1,3,5(10)-triene-9,17-dione.

EXAMPLE 4

Production of compounds XVII, XVIII, XIX and XX from bile with Pseudomonas sp. ATCC 31753.

The seed innoculum is prepared as in Example 1, but using Pseudomonas sp. ATCC 31753. The bile medium is prepared as in Example 1. The innoculated medium is incubated at 30° C. and aeration at 60 ml per minute for 14 hours and then at 200 ml per minute for a further 8 hours. The point of harvesting is chosen when the glycocholic acid in the medium is reduced to 10% of that initially present, as determined by HPLC or t.l.c. The transformed bile is then applied to the polymeric non-ionic adsorbent as in Example 1. All products are washed from the adsorbent with methanol containing 0.1M $NH_3$. The evaporated eluate was extracted with $Na_2CO_3$ to remove acidic material which is separated from the non-acidic material by extraction with chloroform. The acidic products are then recovered by treatment of the aqueous alkaline solution with excess acetic acid and extraction with chloroform, from which the acids (10 g) are recovered by evaporation of the solvent and residual acetic acid.

These acids are converted to their methyl esters with excess diazomethane, which are then recovered by evaporation of the solvent to give crude methyl esters (10.2 g). These methyl esters are dissolved in methylene chloride-ethyl acetate and chromatographed on a column of silica gel with ethyl acetate, methylene chloride and ethanol as solvents.

From an eluate comprising 80% ethyl acetate in methylene chloride a crystalline product is obtained which is seen by t.l.c. to contain XVII. This product is re-chromatographed on silica gel using hexane-ethyl acetate-ethanol as eluents. The eluate comprising 80% ethyl acetate in hexane is seen to contain the methyl ester of XVII. On recovering and recrystallising from ethyl acetate-ethanol pure XVII ester is obtained seen to be methyl 7α,12α-dihydroxy-3-oxopregn-4-ene-20-carboxylate, melting point 220°–2° C. (0.2 g).

Similarly the eluate comprising 5% ethanol in ethyl acetate is seen to contain the ester of XVIII. This product is re-chromatographed on silica gel G with methanol and chloroform as eluents. The eluate comprising 3% methanol is seen to contain the methyl ester of XVIII. On recovering and recrystallising from methanol-chloroform pure XVIII ester is obtained, seen to be methyl 7α,12α-dihydroxy-3-oxopregna-1,4-diene-20-carboxylate, melting point 265°–70° C. with decomposition (0.4 g).

Similarly the eluate comprising 45% ethyl acetate is seen to contain the esters of XIX and XX. This is recovered and re-chromatographed using hexane and ethyl acetate as solvents. The eluate comprising 50% ethyl acetate yields XIX ester which on recrystallising from ethyl acetate-ethanol gives pure XIX ester seen to be methyl 12α-hydroxy-3-oxopregn-4-ene-20-carboxylate, melting point 225°–7° C. (0.51 g). The eluate comprising 55% ethyl acetate yields XX ester which on recrystallising from ethanol gives pure XX ester shown to be methyl 12α-hydroxy-3-oxopregna-1,4-diene-20-carboxylate, melting point 244°–6° C. (0.16 g).

EXAMPLE 5

Production of compounds XVI, XVII, XIX, XXI, XXII and XXIII from bile with Nocardia/Rhodococcus sp. ATCC 31754.

The seed innoculum of Nocardia sp. ATCC 31754 is grown in sterile medium of the same composition used in Example 1. The sterile medium in a suitable flask is innoculated with cells of Nocardia sp. ATCC 31754 grown on a slope culture. The seed innoculum is grown for 36 hours on a shaking bath at 30° C. This seed culture is innoculated aseptically into a fermenter which contains ten to twenty times the volume of the innoculum of a sterile medium of the following composition, per liter of medium Bile concentrate—4 g
$K_2HPO_4$—3.5 g
$KH_2PO_4$—1.5 g
$(NH_4)_2SO_4$—5 g
$MgSO_4.7H_2O$—1 g
$CaCl_2$—0.01 g
$FeSO_4.7H_2O$—0.001 g
Yeast extract—0.1 g
Tap water to—1 liter The innoculated bile medium of 10 liters volume is incubated at 30° C. with agitation and aerated with sterile air at 1.5 liters per minute for 30 hours and then at 1.0 liters per minute until complete after some 55 hours. The products are harvested when cholic acid can no longer be detected in the medium and when the absorption at 240 nm of a clear filtrate is at the maximum value. The transformed bile is applied to the polymeric non-ionic adsorbent column as in Example 1 and washed free of phosphate. The products are eluted with water-methanol mixtures.

From eluate comprising 50 to 100% methanol is obtained, after evaporation of solvent, material which after acidification and extraction into chloroform provides product A (21.0 g). From eluate comprising methanol containing 2% strong ammonia solution is obtained, after similar acidification and solvent removal, product B (1.4 g).

From the chromatography of product B methyl esters in the above way a first fraction is seen to contain XXII ester and on recovering and recrystallising from ethyl acetate gives pure XXII ester seen to be methyl 3,12-dioxopregn-4-ene-20-carboxylate melting point 201°–2° C. (0.65 g). Similarly a subsequent eluate is seen to contain XXIII ester and yields, on recrystallising from ethyl acetate, pure XXIII ester, seen to be methyl 3,12-dioxopregna-4,6-diene-20-carboxylate, melting point 181°–2° C. (0.24 g). A further eluate is similarly obtained and seen to contain XIX ester which on recovery and on recrystallising from ethyl acetate-ethanol gives pure crystals of XIX ester, seen to be methyl 12α-hydroxy-3-oxopregn-4-ene-20-carboxylate melting point 225°–7° C. (0.14 g).

From the chromatography of Product A methyl esters in this way eluate containing XXI esters is obtained which on recrystallising from ethanol-ethyl acetate provides pure crystals of XXI ester seen to be methyl 7α-hydroxy-3,12-dioxopregn-4-ene-20-carboxylate, melting point 258°–60° C. (2.1 g). A further eluate containing XVII ester is obtained which on recrystallising from ethanol-ethyl acetate provides pure crystals of XVII ester seen to be methyl 7α,12α-dihydroxy-3-oxo-pregn-4-ene-20-carboxylate melting point 217°–19° C. (3.8 g).

We claim:

1. A process for the fermentation of bile which includes the steps of:
   (1) cultivating one or more aerobic microorganisms selected from the group consisting of Rhodococcus, Pseudomonas, and Nocardia which has or have the ability to selectively degrade bile acids or bile acid conjugates contained in bile in a cultivation medium containing unfractionated bile as the sole cultivation medium under aerobic conditions while selectively varying the rate of aeration of the cultivation medium within the range of about 40 ml per minute per 10 liters to 1.5 liters per minute per 10 liters, to prepare a compound of the formula:

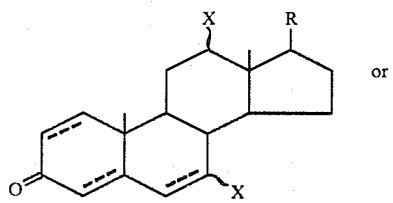

or

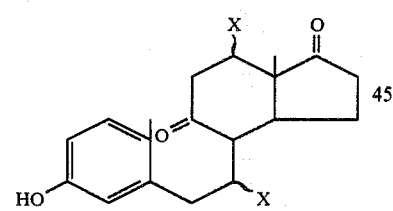

where ~ is a bond which is alpha or beta to the ring, X is hydrogen, hydroxyl or oxo, === may be either a double or single bond, and R is oxo, hydroxy or a propionic acid residue attached at the 2-position, and
   (2) isolating the compound so produced.

2. A process as claimed in claim 1 wherein the cultivation medium includes up to 10% by weight of bile solids.

3. A process as claimed in claim 1 wherein the cultivating step is carried out at a temperature of from 10°–45° C.

4. A process as claimed in claim 3 wherein the cultivating step is carried out at a temperature of from 25°–30° C.

5. A process as claimed in claim 1 wherein the bile culture is harvested by centrifugation followed by acidification of the remaining liquor, extraction with a water-immiscible organic solvent and fractionation of the extract by crystallisation or chromatographic means to isolate the desired compound(s).

6. A process as claimed in claim 1 wherein the harvesting step includes centrifugation to remove unwanted bacterial cells, percolating the liquor through a column of porous polymer beads, washing the column to remove unwanted inorganic compounds, and isolation of the desired compound by eluting the column with a mixture of water and methanol and subsequent crystallisation from suitable solvents.

7. A process as claimed in claim 1 wherein a compound of formula

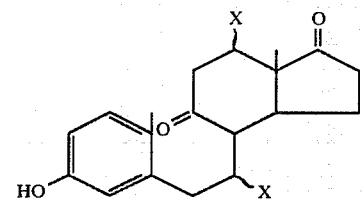

wherein X in at least one position is hydroxyl is obtained by cultivating Pseudomonas in the cultivation medium.

8. A process is claimed in claim 1 wherein a compound of formula

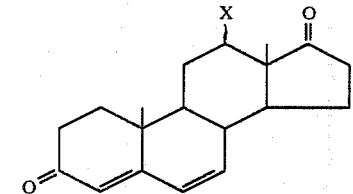

is obtained by cultivating Pseudomonas in the cultivation medium.

9. A process as claimed in claim 1 wherein a compound of formula

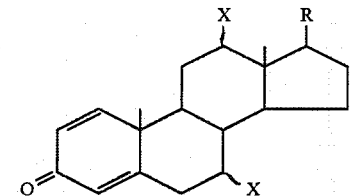

is obtained by cultivating Pseudomonas in the cultivation medium.

10. A process as claimed in claim 1 wherein a compound of formula

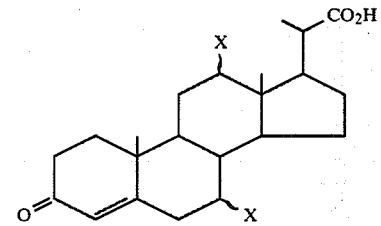

is prepared by cultivating Rhodococcus sp. ATCC 31754 in the cultivation medium.

11. A process as claimed in claim 1 wherein a compound of formula

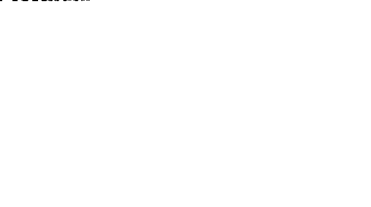

is prepared by cultivating Pseudomonas sp. ATCC 31752 or 31753 in the cultivation medium.

12. A process as claimed in claim 1 wherein a compound of formula

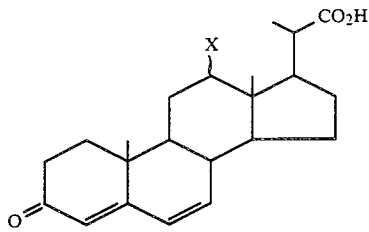

in the case of X being hydroxyl is prepared by cultivating Pseudomonas or Rhodococcus in the cultivation medium but in the case of X being oxo is prepared by cultivating Rhodococcus in the cultivation medium.

13. A process as claimed in claim 1 wherein a compound of formula

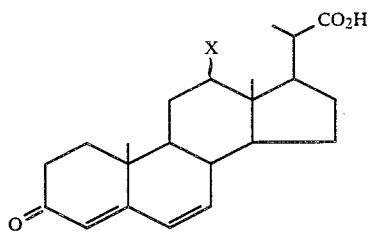

is prepared by cultivating Pseudomonas sp. ATCC 31752 or Nocardia sp. ATCC 31754 in the cultivation medium.

* * * * *

UNITED STATES PATENT AND TRADEMARK OFFICE
CERTIFICATE OF CORRECTION

PATENT NO. : 4,528,272

DATED : Jul. 9, 1985

INVENTOR(S) : PARK ET AL.

It is certified that error appears in the above-identified patent and that said Letters Patent is hereby corrected as shown below:

On the cover sheet, insert:

--[30]     Foreign Application Priority Data

February 22, 1980 [AU]     Australia ........................PE.2498--

Signed and Sealed this

Twenty-ninth Day of October 1985

[SEAL]

Attest:

Attesting Officer

DONALD J. QUIGG

Commissioner of Patents and Trademarks—Designate